United States Patent [19]
Nakamura

[11] Patent Number: 5,330,462
[45] Date of Patent: Jul. 19, 1994

[54] MULTIPLE BAG

[75] Inventor: Yasushi Nakamura, Fujinomiya, Japan

[73] Assignee: Terumo Kabushiki Kaisha, Tokyo, Japan

[21] Appl. No.: 771,304

[22] Filed: Oct. 2, 1991

[30] Foreign Application Priority Data

Oct. 5, 1990 [JP] Japan ................ 2-267873

[51] Int. Cl.⁵ .............................. A61M 5/00
[52] U.S. Cl. .................... 604/410; 604/408; 604/403
[58] Field of Search ................ 604/408–416

[56] References Cited

U.S. PATENT DOCUMENTS

| | | |
|---|---|---|
| 3,431,890 | 3/1969 | Ulary . |
| 4,222,379 | 9/1980 | Smith . |
| 4,223,675 | 9/1980 | Williams ............... 604/410 |
| 4,507,123 | 3/1985 | Yoshida . |
| 4,810,378 | 3/1989 | Carmen et al. ........... 604/410 |
| 4,938,758 | 7/1990 | Al-Sioufi ............... 604/410 |

FOREIGN PATENT DOCUMENTS

| | | |
|---|---|---|
| 0095526 | 12/1983 | European Pat. Off. . |
| 0366554 | 5/1990 | European Pat. Off. . |
| 2439589 | 5/1980 | France . |
| 8904639 | 6/1989 | PCT Int'l Appl. ........... 604/410 |
| WO92/20013 | 11/1992 | World Int. Prop. O. . |

OTHER PUBLICATIONS

Patent Abstracts of Japan, vol. 13, No. 355 (P-914) Aug. 9, 1989 & JP-A-01 113 766 (Richoh) May 2, 1989.
Patent Abstracts of Japan, vol. 12, No. 156 (P-701) May 13, 1988 & JP-A-62 273 537 (Konishiroku Photo Ind.) Nov. 27, 1987.

Primary Examiner—Robert A. Hafer
Assistant Examiner—Sam Rimell
Attorney, Agent, or Firm—Frishauf, Holtz, Goodman & Woodward

[57] ABSTRACT

A multiple bag comprising a plurality of bags including a chemical containing bag charged with liquid chemical and at least one vacant bag, wherein the inner surface of the chemical containing bag is less rough than that of the vacant bag.

4 Claims, 1 Drawing Sheet

MULTIPLE BAG

BACKGROUND OF THE INVENTION

1. Field of the Invention

The present invention relates to a multiple bag (or container) comprising a plurality of bags which are linked with each other. The multiple bag is used, for example, as a blood bag for separating whole blood into blood constituents.

2. Description of the Related Art

For the reason of an effective utilization of blood and reduction of physical load with which a patient to be transfused may be burdened, the blood transfusion system now in use comprises steps of centrifugally separating whole blood obtained from a donor into different constituents and transfusing only necessary constituents to the patient. The introduction of such a constituent transfusion system permits more effective use of blood than in the conventional system utilizing unseparated whole blood.

A multiple bag comprising a donor bag (a blood collection bag) and one or more different bags is used in the constituent transfusion.

For example, a triple bag comprised of a blood collecting bag, a platelet concentrate bag (hereinafter referred to as PC bag) for preserving platelet and a plasma preserving bag (hereinafter referred to as plasma bag), these bags being connected with each other by tubes. A blood collected in the blood collection bag is subjected twice to centrifugal separation to be separated into three different constituents such as erythrocyte component, thick platelets component, and thin platelets component, and these constituents are contained for preservation in the donor bag, PC bag, and plasma bag respectively.

The respective bags constituting such a multiple bag are produced by overlaying sheet materials of soft polyvinyl chloride, and fusion bonding them together at the peripheral edges, and these bags are generally subject to high-temperature and high-pressure steam sterilization (autoclave sterilization). In order to avoid any blocking which may occur between the inner surfaces of the opposite sheets of the bags during the autoclave sterilization, the sheets are treated for embossing so that they may have a surface roughness (Rz) ranging around from 15 $\mu$m to 50 $\mu$m.

In view of the production control and cost as well, these bags are produced from the same sheet materials.

with such a multiple bag, there lies problems that it gives rise to adhesion of the blood constituents (erythracyte, leukocyte, platelet) to the inner surface of the bag sheet, and to excessive remaining of blood within the bag when the blood is removed.

An earnest and deep study by the present inventor of these phenomena revealed that such phenomena are considerably observed if the inner surface of the bag sheet is subjected to deeper embossment, or fine projections are formed more greatly in height on the inner surface of the sheet.

In this connection, it seems effective to use a sheet with the inner face having fine projections of less height or being less rough. In the case, however, it causes insufficient preventive effect of blocking between the sheets on the contrary.

SUMMARY OF THE INVENTION

The object of the present invention is to provide a multiple bag wherein the blocking between the sheets of the bags can be prevented, and with regard to the liquid-chemical containing bag, the adhesion of the hemocyte to the inner face of the bag sheets can be reduced, resulting in that the residual of blood or its constituents (hereinafter referred to as blood residual) left within the bag during removal of the blood can be suppressed.

Such an object may be achieved by a multiple bag of the present invention, which comprises a plurality of bags including a chemical containing bag charged with liquid chemical and at least one vacant bag, wherein the inner surface of said chemical containing bag is less rough than that of said vacant bag.

In the present invention, it is preferable that roughness (Rz) of the inner surface of said chemical containing bag is from 2 $\mu$m to 15 $\mu$m. Rz means an average roughness of 10 points in the predetermined length.

In addition, it is preferable that an amount of liquid charged in the chemical containing bag is equal to 5 to 65% of the volume of the bag.

In general, the blood collection bag (donor bag) in the multiple bag is filled in advance with liquid anticoagulants (chemicals) such as solutions of ACD, CPD, CPDA-1, sodium heparinate. An inventor's study has clearly revealed that blocking due to the autoclave sterilization may be avoided even if the surface roughness of the inner surface of the sheet of such a chemical containing bag is more reduced than the conventional one.

It is assumed that the liquid chemical charged within the bag forms a liquid layer between the inner surface of the opposed sheets, and the liquid layer has the function of preventing the adhesion of the sheets to each other. Such a function is relevant to the amount of chemicals contained in the bag.

In accordance with the present invention, the vacant bag containing no liquid chemicals is made of sheets having the same surface roughness as the conventional one so as to obtain the preventive effect of blocking, and the chemical containing bag such as the blood collecting bag (donor bag) is made of sheet materials having the inner surface roughness less than that of said vacant bag. Preferably, the inner surface of the donor bag has roughness (Rz) ranging from 2 $\mu$m to 15 $\mu$m. As a result of the above construction, the adhesion of the hemocyte to the inner face of the donor bag sheet as well as the residual of the blood within the bag may be suppressed, and besides, a sufficient preventive effect of blocking can be achieved.

The accompanying drawing, which is incorporated in and constitutes a part of the specification, illustrates a presently preferred embodiment of the invention and, together with the general description given above and the detailed description of the preferred embodiment given below, serves to explain the principles of the invention.

BRIEF DESCRIPTION OF THE DRAWINGS

The accompanying drawing, which is incorporated in and constitutes a part of the specification, illustrates a presently preferred embodiment of the invention and, together with the general description given above and the detailed description of the preferred embodiment given below, serves to explain the principles of the invention.

DETAILED DESCRIPTION OF THE PREFERRED EMBODIMENTS

Figure 1:
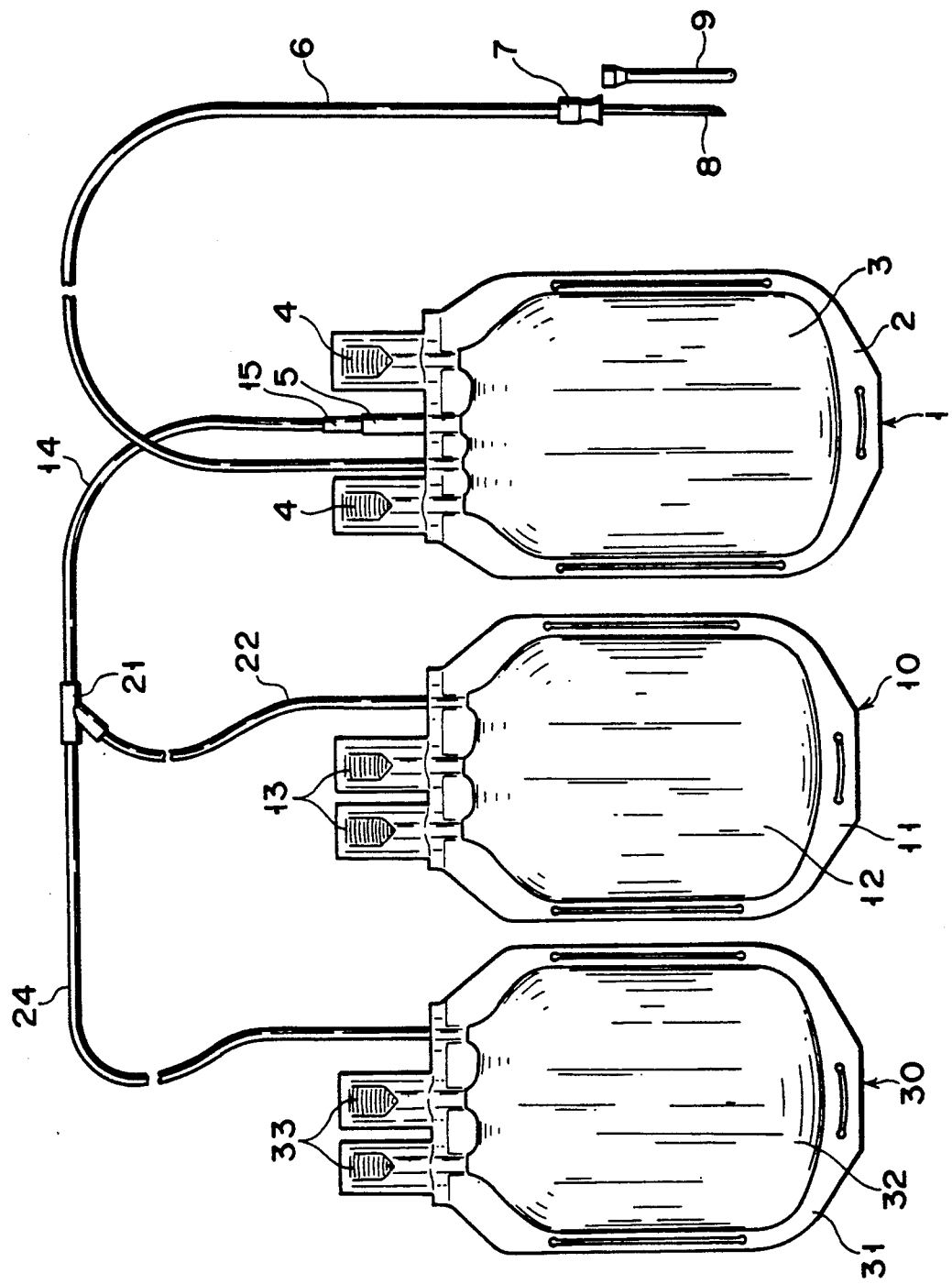
FIG. 1 is a plan view showing the structure of the multiple bag in accordance with the present invention.

Now, the multiple bag in accordance with the present invention will be described in more detail with reference to a preferred embodiment as shown in the accompanied drawing.

FIG. 1 illustrates an embodiment of the multiple bag according to the present invention. This multiple bag is a triple bag comprising a blood collecting bag (donor bag), a platelet concentrate (PC) bag, and a plasma containing bag, all connected to each other by means of tubes.

In the drawing, the blood collection bag 1 located at the right hand is produced by placing two sheets made of, preferably, soft polyvinyl chloride (PVC) one upon another and fusing the sheets at the sealed peripheral portions 2 by high-frequency heating or other heating process.

A blood storing portion 3 for containing collected blood or thick erythrocyte centrifugally separated from the whole blood is formed within an area enclosed with the sealed portion 2.

The blood collecting bag 1 has two outlets 4, 4 provided with stoppers (peel tab) on the upper part thereof, and an outlet 5 formed between said outlets 4, 4 for connecting with other bags which will be described later.

The outlet 5 is connected to one end of a flexible tube 14 by using a connecting member 15.

The other end of tube 14 is connected to a three way connector 21. This connector 21 is made by molding of, for example, polyvinyl chloride or polycarbonate resins.

Note that connecting member 15 should preferably be a member which is adapted to close the passage before it is broken, and to open the passage upon the breakage; an example of such member is the click chip available from Terumo Kabushiki Kaisha.

Furthermore, the upper portion of the blood collecting bag 1 is connected to one end of a flexible tube 6 in such a manner that the tube 6 communicates with the blood storing portion 3. The other end of the tube 16 is provided with a blood collecting needle 8 via a hub 7. The hub 7 has a cap 9 which covers the blood collecting needle 8 as desired.

This blood collection bag 1 holds liquid ant-coagulants such as ACD (acid-dextrose), CPD ( citrate-phosphate-dextrose), CPAD-1 (citrate-phosphate-adenine-dextrose), sodium heparinate within the blood containing portion 3. Thus, the blood collection bag 1 serves as a chemical containing bag of the present invention.

In this case, it is desirable that the blood collecting bag 1 contain the amount of the liquid chemicals corresponding to 5 to 65%, or more preferably 10 to 65% of the volume of the bag 1; if less than 5%, the liquid chemicals prove to be less effective and cause decrease in its preventive effect of blocking, and when exceeds over 65%, the content of chemicals is too high, thus resulting in decrease in efficiency of blood collection.

In the drawing, the PC bag 10 may be preferably produced by stacking two sheets of soft flexible polyvinyl chloride one upon another and fusing them at sealed edge portions 11 through the high-frequency heating or other heating process.

A platelet storing portion 12 for containing a platelet separated from the whole blood in the blood collecting bag 1 is formed within an area enclosed with the sealed portion 11.

The PC bag 10 has two outlets 13, 13 each provided with stoppers (peal tab) on the upper part thereof.

Additionally, there is provided a flexible tube 22 communicating with the platelet storing portion 12. One end of the tube 22 is connected to the upper portion of the PC bag 10 near the outlets 13, while the other end is connected to one end of said three way connector 21. This arrangement provides communication of the blood storing portion 3 of the blood collection bag 1 with the platelet storing portion 12 of the PC bag 10 via the tubes 14, 22 and the three way connector 21.

In the drawing, a plasma bag 30 positioned on the left hand should preferably be produced by stacking two sheets of soft polyvinyl chloride one upon another and fusing them together at sealed edge portions by high-frequency heating or other heating process.

A plasma storing portion 32 for containing plasma (particularly, plasma with poor platelet) separated from the whole blood is formed within the area enclosed with the sealed edge portion 31.

Two outlets 33, 33 provided with stoppers (peal tab) are formed on the upper portion of the plasma bag 30.

One end of a flexible tube 24 is connected to the upper portion near the outlets 33 so as to communicate with the plasma storing containing portion 32.

The other end of the tube 24 is connected with the other end of said three way connector 21. This arrangement provides communication of the plasma storing portion 32 of the plasma bag 30 with the blood storing containing portion 3 of the blood collection bag 1 as well as with the platelet storing portion 12 of the PC bag 10 via the tubes 14, 22, 24 and three way connector 21.

Liquid chemicals are neither contained in the platelet storing portion 12 of the PC bag 10 nor in the plasma storing portion 32 of the plasma bag 30. Therefore, the PC bag 10 and the plasma bag 30 are vacant bags of the present invention.

However, the platelet storing portion 12 of the PC bag 10 may be charged with an erythrocyte preservative agent (liquid chemical). In such a case, the PC bag 10 is a chemical containing bag of the present invention.

Such an erythrocyte preservative agent involves, for example, SAGM liquid which is an aqueous solution containing 0.877% of sodium chloride, 0.0169% of adenine, 0.818% of dextrose, and 0.525% of D-mannitol.

The optimum amount of such erythrocyte preservative agent is the same as the in the case of said liquid anticoagulant.

With reference to the chemical containing bag as represented by said blood collecting bag 1 and the vacant bag as represented by said plasma bag 30 in accordance with the present invention, the sheets of which those bags are made are different from each other in the roughness of the inner surfaces.

That is, the roughness of the inner surface of the chemical containing bag is less than that of the vacant bag.

Such a structure ensures the suppression of adhesion of the hemocyte to the inner surface of the chemical containing bag, and a decrease of blood residual during discharge. In addition, the prevention of a blocking between the sheets of the chemical containing bag can be effectively achieved due to the existence of the liquid chemicals, during autoclave sterilization.

In this case, it is desired that the inner surface of each sheet of the chemical containing bag is as rough as around 2 to 15 μm (Rz), preferably around 5 to 15 μm (Rz). Note that Rz means an average roughness among ten points. A surface roughness less than 2 μm (Rz) tends to deteriorate the preventive effect of blocking. On the contrary, if the roughness exceeds 15 μm (Rz), the adhesion of the hemocytes to the inner surface of the bag sheet would be considerably high, thus resulting in a considerable amount of the blood remaining within the bag.

Only one requirement for the inner surface of each sheet of the vacant bag is that it is rougher than that of each sheet of the chemical containing bag, although the Rz Value thereof is not specifically limited. It is desirable, however, that the surface roughness is not less than about 10 μm, more preferably, of the order of 15 to 50 μm.

With no specific limitation, the sheet of the respective bags 1, 10 and 30 are preferably as thick as around 0.1 to 0.8 mm, and more preferably, around 0.2 to 0.6 mm.

The description of the multiple bag in accordance with the present invention has been made with reference to the triple bag as illustrated, but the present invention is not limited thereto.

For example, a variation of the multiple bag may take the form of a triple bag consisting of bags for different applications, a double bag composed of a blood collection bag and a PC bag connected to each other, or said triple bag or double bag to which is added one or more other bags such as, for example, a bag for recovering cryoprecipitate (AHF), a bag for preserving erythrocyte, a bag for removing leukocyte, or a filter.

It will be noted that the connection mode between the tubes is not also limited to that illustrated.

Now, the present invention will be further described in detail with reference to the experimental examples.

The following are the experimental methods.

Firstly, 50 parts by weight of dioctyl phthalate (DOP) as a plasticizer, 10 parts by weight of epoxidated soybean oil, and 0.1 parts by weight of Ca-Zn series stabilizer are combined with reference to 100 parts by weight of polyvinyl chloride resin to prepare sheet materials having a thickness of 0.4 mm.

The resultant sheet materials are subjected to embossment so that fine projections each having different heights may be formed on one side of the sheets. The roughnesses of the finished surfaces are shown in the following table.

Next, two pieces of said sheets are placed one upon another with said finished surfaces on the inside, and then the peripheral portions are sealed by the high-frequency fusion with the result that a blood collecting bag (an internal volume of 200 ml) a PC bag (an internal volume of 150 ml), and a plasma bag (an internal volume of 150 ml) have been obtained.

Of these bags, the blood collecting bag is filled with 28 ml (which is equal to 14% of the bag volume) of a CPD liquid as an anticoagulant so as to act as a chemical containing bag, while the PC bag and plasma bag are rendered vacant.

The blood collection bag, PC bag and plasma bag are connected with each other by means of a tube of polyvinyl chloride having an inner diameter of 3 mm and a three way connector so as to provide communication between the inner sides of the respective bags, thus resulting in a formation of a triple bag with such a construction as shown in FIG. 1 (Embodiments 1 to 4, Comparative Examples 1, 2).

In accordance with the Embodiment 4, the PC bag is filled with 10 ml (equal to 10% of the bag volume) of an SAGM liquid as a preservative agent for erythrocyte so as to serve as a chemical containing bag.

These bags were subjected to autoclave sterilization at a temperature of 121° C. for 30 minutes.

After the sterilization, an examination was carried out to see whether or not the blocking took place between the internal faces of the sheets of the bags. The results are shown in the following table. The results are evaluated in the following manners.

Evaluation

⊚ : No blocking occurred

○ : Some has been subject to blocking, but easily separable by peeling

Δ : Some has been so subject to blocking as to render separation difficult

X : Blocking occurred overall so that separation is difficult.

The following tests were performed in order to determine preserving performance for blood and discharging performance for blood.

1) Test for adherence of erythrocyte

A total of 200 ml of blood from a donor had been gathered in the blood collection bags of said triple bag, and centrifugally processed to obtain platelet concentrate plasma (PC). The resulted PC was transferred to a vacant PC bag and preserved there at 22° C. for a period of 3 days.

Additionally, 200 ml of blood were collected from the same donor and introduced into said triple bag, and preserved at 4° C. for as long as 21 days.

After the preservation, sample pieces (10 mm × 10 mm) were cut out from the respective bags, then adhered blood components were fixed by glutaric aldehyde, then subjected to dehydration with alcohol, and the number of adhered hemocytes was counted based on 10 pieces as a unit by using an electronic microscope. The result will be shown in the Table 1.

2) Test for blood residual 200 ml of blood were collected from a donor and introduced into the blood collection bag of said triple bags, and after a lapse of 5 minutes, the total amount of the blood was discharged in the manner of gravity-drop from the outlets of the bags.

After the discharge, the measurement was carried out to determine the amount of the blood residual within the blood collecting bag.

The result is shown in the Table 1.

TABLE 1

| | | Surface roughness of inner surface of sheet Rz (μm) | Evaluation of blocking occurred | Adherence of hemocytes (piece/mm²) | Blood residual (g) |
|---|---|---|---|---|---|
| Embodiment 1 | Blood collecting bag | 2 | ○ | 3 | 0.5 |
| | PC bag | 15 | ⊙ | 250 | — |
| | Plasma bag | 15 | ⊙ | — | — |
| Embodiment 2 | Blood collecting bag | 5 | ⊙ | 3 | 0.6 |
| | PC bag | 15 | ⊙ | 250 | — |
| | Plasma bag | 10 | ○ | — | — |
| Embodiment 3 | Blood collecting bag | 13 | ⊙ | 3 | 0.8 |
| | PC bag | 15 | ⊙ | 250 | — |
| | Plasma bag | 15 | ⊙ | — | — |
| Embodiment 4 | Blood collecting bag | 5 | ⊙ | 3 | 0.6 |
| | PC bag | 15 | ⊙ | 200 | — |
| | Plasma bag | 15 | ⊙ | — | — |
| Comparative Example 1 | Blood collecting bag | 5 | ⊙ | 3 | 0.6 |
| | PC bag | 5 | X | 150 | — |
| | Plasma bag | 5 | X | — | — |
| Comparative Example 2 | Blood collecting bag | 20 | ⊙ | 7 | 1.3 |
| | PC bag | 20 | ⊙ | 280 | — |
| | Plasma bag | 20 | ⊙ | — | — |

The above table shows that in accordance with the Embodiments 1–4 of the present invention, the blockings between the sheets of the respective bags had been prevented, and the adhesion of hemocytes to the inner side of the chemical containing bags and the blood residual were preferably suppressed.

As described above, in accordance with the present invention, the blocking between the sheets of the bags can be prevented. Further, the adhesion of blood constituents to the inner surface of the sheets can be suppressed and the blood residual occurring when the blood or its constituents are discharged from the bags can be reduced.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A multiple bag assembly, comprising: a plurality of interconnected bags;
   said interconnected bag including a chemical containing blood collecting bag charged with a liquid chemical and at least one vacant bag;
   said chemical containing blood collecting bag having an inner surface with a first roughness and said at least one vacant bag having an inner surface with a second roughness, said first roughness being less than said second roughness;
   said first roughness of said inner surface of said chemical containing blood collecting bag being in the range of 2 μm to 15 μm in terms of Rz; and
   said second roughness of said inner surface of said at least one vacant bag being in the range of approximately 15 μm to 50 μm in terms of Rz.

2. A multiple bag assembly as defined in claim 1, wherein an amount of said liquid chemical charged in said chemical containing blood collecting bag is equal to 5 to 65% of the volume of the chemical containing blood collecting bag.

3. A multiple bag assembly as defined in claim 1, wherein said liquid chemical is selected from the group consisting of anti-coagulants and preservatives for erythrocytes.

4. A multiple bag assembly, comprising:
   a plurality of interconnected bags;
   said interconnected bags including a chemical containing blood collecting bag charged with a liquid chemical and at least one vacant bag;
   said chemical containing blood collecting bag having an inner surface with a first roughness and said at least one vacant bag having an inner surface with a second roughness, said first roughness being less than said second roughness;
   said first roughness of said inner surface of said chemical containing blood collecting bag being in the range of 2 μm to 15 μm in terms of Rz;
   said second roughness of said inner surface of said at least one vacant bag being in the range of approximately 15 μm to 50 μm in terms of Rz;
   an amount of said liquid chemical charged in said chemical containing bag is equal to 5 to 65% of the volume of the chemical containing bag;
   wherein said liquid chemical is selected from the group consisting of anti-coagulants and preservatives for erythrocytes.

* * * * *